United States Patent [19]

Wohlgemuth

[11] Patent Number: 4,482,324
[45] Date of Patent: Nov. 13, 1984

[54] PERCUSSION INSTRUMENT

[75] Inventor: Jürgen Wohlgemuth, Darmstadt, Fed. Rep. of Germany

[73] Assignee: Siemens Aktiengesellschaft, Berlin & Munich, Fed. Rep. of Germany

[21] Appl. No.: 480,320

[22] Filed: Mar. 30, 1983

[30] Foreign Application Priority Data

Apr. 26, 1982 [DE] Fed. Rep. of Germany ....... 3215498

[51] Int. Cl.$^3$ .............................................. A61C 5/00
[52] U.S. Cl. ..................... 433/215; 433/72; 433/121; 433/29; 128/776; 173/120
[58] Field of Search ............... 433/215, 72, 121, 75, 433/27, 118, 124, 150, 151, 164, 29; 128/776; 173/94, 95, 117, 119, 120; 81/464, 465, 466

[56] References Cited

U.S. PATENT DOCUMENTS

| 165,701 | 7/1875 | Bilharz | 433/124 |
|---|---|---|---|
| 734,387 | 7/1903 | Woodworth | 173/117 |
| 3,094,115 | 6/1963 | Polin | 433/215 |
| 3,653,373 | 4/1972 | Batterman | 128/776 |
| 3,683,503 | 8/1972 | Klein | 433/29 |
| 3,782,188 | 1/1974 | Korber et al. | 128/776 |
| 3,972,122 | 8/1976 | Sutter | 433/118 |
| 4,034,476 | 7/1977 | Johnson | 433/27 |
| 4,058,115 | 11/1977 | Forster | 128/776 |
| 4,192,321 | 3/1980 | Korber et al. | 128/776 |
| 4,340,069 | 7/1982 | Yeaple | 433/72 |

FOREIGN PATENT DOCUMENTS

| 498728 | 5/1930 | Fed. Rep. of Germany | 173/117 |
|---|---|---|---|
| 2853252 | 6/1980 | Fed. Rep. of Germany | 128/776 |
| 2617779 | 2/1982 | Fed. Rep. of Germany | 433/216 |

Primary Examiner—John J. Wilson
Attorney, Agent, or Firm—Hill, Van Santen, Steadman & Simpson

[57] ABSTRACT

A percussion instrument suitable for use in dental practice for determining the degree of looseness of a tooth has a ram displacably seated in the handpiece and a means for accelerating the ram from an initial position to a defined velocity, the ram subsequently moving toward a test object in free flight with a constant velocity. The ram is returned to its initial position with the assistance of a magnetic field. The ram is in the form of an elongated oscillating lever having a pivot axis located at its center of gravity, the axis being disposed at a right angle relative to a longitudinal axis of the instrument. The ram has a test head at one end thereof which is disposed at an angle, such as a right angle, with respect to the lever portion of the ram.

15 Claims, 6 Drawing Figures

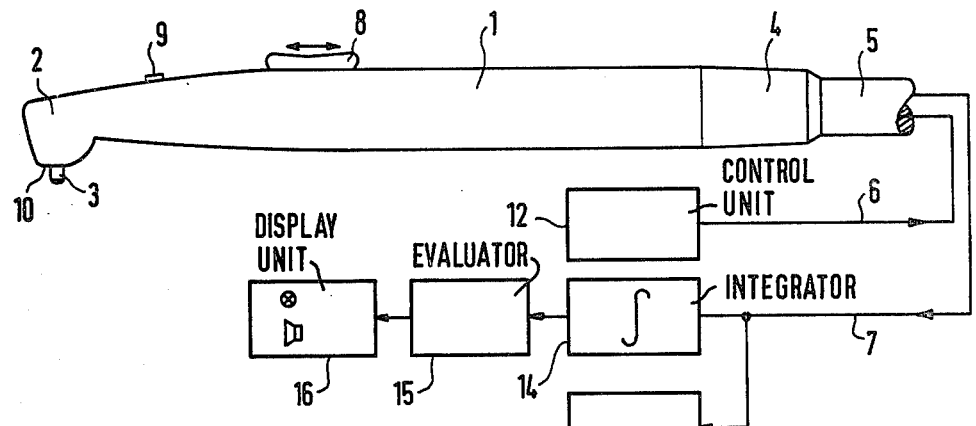
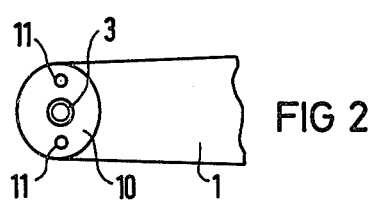
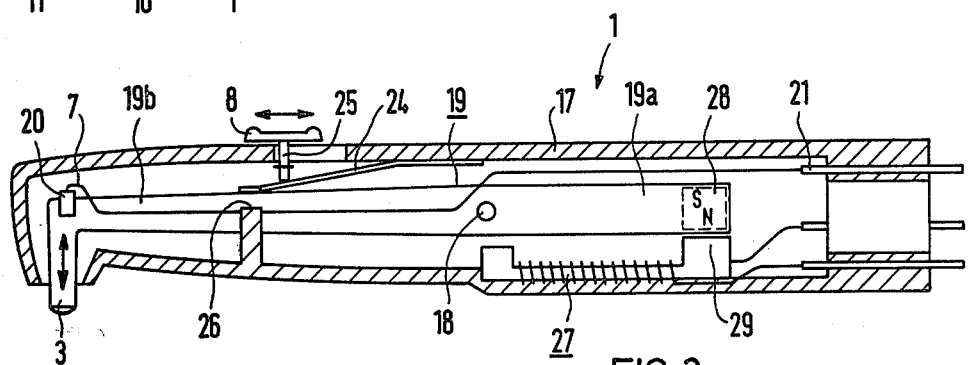
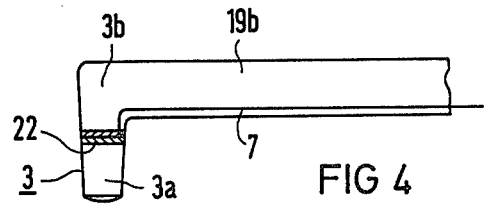

PERCUSSION INSTRUMENT

BACKGROUND OF THE INVENTION

1. Field of the Invention

The present invention relates to percussion instruments of the type suitable for use in dental practice for determining the degree of looseness of a tooth, and in particular to such a percussion instrument having a ram displacably seated in a handpiece and a means for accelerating the ram to a specific velocity from an initial position, the ram subsequently moving toward a test object in free flight decoupled from its drive means at a constant velocity, and a magnetic means for returning the ram to its initial position.

2. Description of the Prior Art

A percussion instrument having a displacably seated ram and a means for accelerating the ram to a specific velocity is disclosed in German OS No. 2,617,779. In this known instrument, the ram is mounted in a housing so as to move longitudinally back and forth in the axial direction of the instrument. The ram is accelerated to a specific velocity by means of a helical spring disposed in a front portion of the instrument, near the free end of the ram carrying a test head. The ram is maintained in its initial position by means of a magnetic coil. After complete relaxation of the spring, the ram separates from the spring and, guided by bearings, approaches the object to be tested with a theoretically constant velocity in free flight. After impact against the object to be tested, the ram is repelled in a direction toward its initial position by the rebound or reactive force arising upon impact. The coil is supplied with a current pulse toward the end of the return motion of the ram such that the ram is returned to its initial position by the magnetic field generated thereby, and the spring is again tensed. An acceleration pickup is connected to the ram by means of a flexturally slack cable for detecting a change in velocity of the ram upon impact of the ram against the object to be tested. This change in velocity is evaluated during the excursion and return paths of the ram for specific test and diagnostic purposes. The velocity change is evaluated in an electronic evaluation unit connected to the acceleration pickup. In dental practice, for example, the velocity of the ram is a direct indicator of the degree of tooth mobility, that is, the degree to which a tooth is loosened in the gum tissue. The time within which the tooth to be tested returns to its initial position after the impact pulse provides useful information regarding the condition of the tooth retaining means.

Conventional percussion instruments of the type described in German OS No. 2,617,779 have several disadvantages. Because the ram executes a substantially straight line flight motion proceeding in the axial direction of the instrument, the velocity of the ram will assume a theoretically constant value only when the instrument is held substantially horizontal so that the ram velocity is not influenced by gravitational force. When the attitude of the instrument departs from the horizontal, the flight velocity of the ram is altered and the measuring results are correspondingly falsified. The only safeguard available to avoid such data falsification in the use of conventional percussion instruments is to hold the instrument absolutely horizontally, requiring a high degree of concentration from the user.

A further disadvantage of such conventional percussion instruments is that the test objects such as, for example, a patient's teeth, can only be subjected to impact from that side of the patient's mouth from which the instrument can be introduced at a horizontal attitude. Test subjects which are not accessible in the direction in which the instrument is introduced to the object to be tested horizontally can therefore not be measured, or at least cannot be reliably measured. In the use of the instrument for examining tooth mobility, teeth in the molar region cannot be reached with a conventional percussion instrument or, if accessible, cannot be accurately tested.

Another disadvantage in conventional percussion instruments of the type described above is the arrangement of the acceleration pickup which generates acceleration signals for determining the ram velocity. The acceleration pickup utilized in conventional percussion instruments is disposed at that end of the ram facing away from the test head and is connected to evaluation electronics by means of a highly flexible lead. Because the lead must participate in the ram movement, that is, be comovable therewith, tearing of the line can occur. Moreover, the acceleration signal obtained with conventional acceleration pickups of this type is relatively small and must be amplified by means of relatively complex circuitry. A further disadvantage is that the ram in conventional devices is seated in common bearings and is decelerated by the frictional forces of the bearings. These frictional forces may vary over time by the action of external influences such as humidity, dust or the like. Thus, the ram velocity is subject to corresponding varying alterations which falsify the test results.

SUMMARY OF THE INVENTION

It is an object of the present invention to provide a percussion instrument having a ram which is accelerated from an initial position to a specific velocity for striking a test object at a constant velocity wherein the ram is an elongated oscillating lever pivotally seated at its center of gravity on a pivot axis disposed at right angles relative to a longitudinal axis of the instrument, and wherein the ram has an angled test head. In a preferred embodiment of the invention the test head is disposed at a right angle relative to the longitudinal axis of the oscillating lever.

A percussion instrument constructed in accordance with the principles of the present invention functions independently of the attitude or inclination of the instrument with respect to the horizontal, so that the ram is uninfluenced by gravity. Moreover, as a result of the angular disposition of the test head, measurements can be undertaken at locations which are relatively inaccessible such as, for example, in the molar area of a patient's teeth.

In a further embodiment of the invention, the acceleration pickup for generating signals which are monitored and evaluated for determining the ram velocity is disposed at a front section of the ram near the test head. Mounting the acceleration pickup at this location has the advantage that a considerably larger acceleration signal upon impact against a test object is obtained, and a lower noise signal during the return path of the ram is obtained in comparison to conventional instruments of this type. Because the ram is mounted sub-stantially friction-free at its center of gravity, the bearing friction experienced by the ram during motion thereof is negligible. Moreover, the placement of the acceleration pickup at a front section of the ram permits the necessary lead cable from the acceleration pickup to be arranged so as to be substantially unstressed during oscillatory motion of the ram, thereby contributing to long cable life.

BRIEF DESCRIPTION OF THE DRAWINGS

FIG. 1 is a side view of a percussion instrument constructed in accordance with the principles of the present invention also including a schematic block diagram of control and evaluation circuitry for use with the instrument;

FIG. 2 is a plan view of the front portion of the instrument shown in FIG. 1 showing the test head and surrounding structure;

FIG. 3 is a sectional view of the instrument shown in FIG. 1 in a first embodiment;

FIG. 4 is a side view of a further embodiment of the device shown in FIG. 1 with an acceleration pickup disposed at the test head;

DESCRIPTION OF THE PREFERRED EMBODIMENTS

Figure 5:
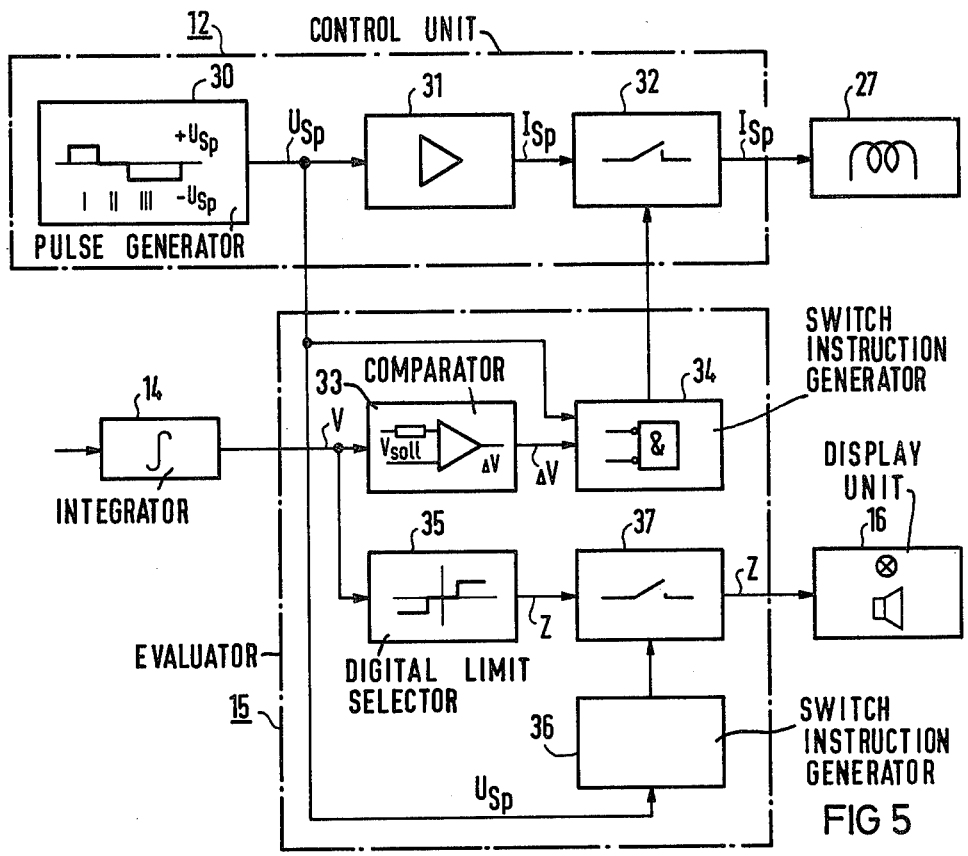
FIG. 5 is a schematic block diagram showing details of the control unit and an evaluator unit for the instrument shown in FIG. 1.

A percussion instrument constructed in accordance with the principles of the present invention is shown in FIG. 1. The instrument includes an elongated drip or handpiece 1 which has a front angled end forming a head housing 2 from which a test head 3 of an oscillating lever (shown in greater detail in the following Figures) projects. A supply line 5 is connected to the opposite end of the handpiece 1 by means of a connection armature 4. The supply line 5 includes leads 6 and 7 connected to control and evaluation circuitry described in greater detail below. The instrument has a finger-actuatable slide 8 and a display lamp 9.

The end face 10 of the head housing 2 is shown in FIG. 2 and exhibits two light sources 11 at its circumference which are arranged so as to supply focused light to a test object, such as a tooth, in the form of a circular light spot in a plane disposed at a right angle relative to the longitudinal axis of the test head 3, that is, the light plane is parallel to the end face 10 of the head housing 2.

The lead 6 is connected to a control unit 12, shown in greater detail in FIG. 5, which supplies periodic current pulses to a drive means disposed inside the handpiece 1.

Acceleration signals, obtained from the test head 3 when it strikes the object to be tested, are supplied via the line 7 to an evaluator 13 and to an integrator 14 for obtaining a velocity signal V according to the relationship $V = \int b \, dt$ (wherein b is the ram acceleration), the velocity signal V being further processed in a measuring and evaluation unit 15. The user can be provided with acoustical or optical information by a display means 16.

The device shown in FIG. 1 is shown in longitudinal section in FIG. 3. In this embodiment, the ram is an elongated oscillating lever 19 having the test head 3 mounted at one end thereof. The lever 19 is pivotably seated in a housing 17 of the handpiece 1 by means of an axle bearing 18 disposed at a right angle relative to the longitudinal axis of the instrument. The pivot point for the lever 19 is disposed at the center of gravity of the lever 19 the axle bearing 18 is suitably mounted utilizing conical bearings or ball bearings such that oscillation of the lever occurs substantially friction-free.

The axle 18 subdivides the oscillating lever 19 into a rear section 19a and a front section 19b which carries the test head 3. The test head is disposed at an angle relative to the lever 19, preferably 90°. The test head 3 has a spherical surface which strikes against the object to be tested. The oscillating lever section 19b is relatively long in comparison to the rear section 19a, such that the test head 3 describes a substantially straight line of approximately 2 through 8 mm in the direction of the arrow during the course of a stroke.

An acceleration pickup 20 is mounted at the test head 3 in direct proximity to the object to be tested. The lead 7 from the acceleration pickup 20 is secured in or to the oscillating lever 19 up to the axle bearing 18 and is conducted away from the oscillating lever 19 at the region of the bearing axle 18 to a connection element 21 disposed at the housing 17. The disposition of the acceleration pickup 20 in direct proximity to the test object has the advantage that, because greatest movement of the lever 19 occurs at that location, the highest acceleration signal can be obtained. The acceleration pickup 20 can thus be very small.

One embodiment for the acceleration pickup is shown in FIG. 4 consisting of two piezo-ceramic wafers or lamina 22 disposed adjacent to each other which subdivide the test head 3 into a relatively low mass section 3a containing the test tip and a section 3b having a considerably higher mass in comparison to the section 3a, which merges into the oscillating lever section 19b. Upon impact of the test head 3 against an object to be tested, substantially the entire mass of the oscillating lever influences the piezo-ceramic elements 22 as inertial forces. As a result, a useful signal increased by several powers of 10 over conventional signals is tapped via the lead 7. Upon return of the oscillating lever 19 to its initial position by abutment against a limitation formed in the housing 17, a slight force is generated, however, because of the relatively small mass of the section 3a, which during the return path of the lever 19 is substantially the only mass influencing the piezo-ceramic elements 22, only a slight noise signal is generated.

A leaf spring 24 secured in the housing 17 is provided as a drive means for the forward motion of the oscillating lever 19, that is, motion toward a test object. The leaf spring 24 presses against the oscillating lever sectin 19b by means of a pin 25 secured to the slide 8. The oscillating lever 19 is thus accelerated out of the idle position shown in FIG. 3 up to the required velocity. When this velocity has been reached, the leaf spring 24 is restrained by a detent 26 disposed on the housing 17 at the side of the oscillating lever 19, such that the leaf spring 24 is uncoupled from the oscillating lever 19. Subsequently, the lever 19 continues to move in free flight with a constant velocity until striking the test object, or striking against another detent.

Return of the oscillating lever 19 to its initial position ensues by means of an electro-magnetic coil 27 which is disposed adjacent to the oscillating lever section 19a, and which is driven by current pulses supplied by the control unit 12. The leaf spring 24 may be substantially pre-stressed by means of the slide 8 and the velocity of the lever 19 can thus be controlled during forward motion thereof.

The above-described drive means for the forward motion of the lever 19 is very simple and requires substantially no control circuitry outlay. It is also possible within the framework of the invention, however, to undertake forward drive of the lever 19 by electro-magnetic means. In such an embodiment of the invention, a permanent magnet 28 (shown in dashed lines in FIG. 3) is disposed at the end of the oscillating lever section 19a, the permanent magnet 28 being aligned with the end of the core 29 of the electro-magnetic coil 27 such that an alternating attractive and repelling effect occurs depending upon the direction of the coil current controlled by the control unit 12.

In describing the details of the circuitry shown in FIG. 5, it will be assumed that the coil 27 functions for both the forward and return drive of the oscillating lever 19.

The control unit 12 includes a pulse generator 30 which supplies a positive voltage ($+U_{SP}$) to the drive coil 27 for a forward motion of the lever 19, and which supplies a negative voltage ($-U_{SP}$) for the return motion. A free flight phase II, during which the oscillating lever 19 is propelled forward without external drive means, is chronologically disposed between the forward motion phase I and the return motion phase III.

An amplifier stage 31 is connected to the output of the pulse generator 30 for supplying a control current $I_{Sp}$ to the drive coil 27 via a switch 32. The switch 32, upon receipt of a control signal from the evaluator 15, interrupts supply of the drive current $I_{Sp}$ to the coil 27 during the forward motion phase I when the oscillating lever 19 reaches its rated velocity. For this purpose, an actual velocity signal V, obtained from the integrator 14, is supplied to a comparator 33 in the evaluator 15. The comparator 33 compares the actual velocity signal V with a rated velocity value $V_{soll}$ and generates a difference signal $\Delta V$. The difference signal $\Delta V$ is supplied to a switch instruction generator 34, to which the output of the pulse generator 30 is also supplied. The switch instruction generator 34 (which may be an AND gate) opens the switch 32 when the difference signal $\Delta V$ is zero and the signal from the pulse generator 30 is greater than zero.

The velocity signal V is simultaneously supplied to a digital limit selector 35 which measures the transgression of permissible fluctuations from the rated velocity during the free flight phase II of the oscillating lever 19. If an impermissible deviation is noted by the digital limit selector 35, a warning signal Z is supplied to the display unit 16 via a switch 37 to inform the user of this circumstance. The display unit 16 may include the indicator or warning light 9 on the handpiece 1.

The switch 37 is controlled by another switch instruction generator 36 which permits the error signal Z to be connected to the display unit 16 only when the oscillating lever 19 is in the free flight phase II. During this phase, the output voltage $U_{SP}$ from the pulse generator 30 is zero.

Figure 6:
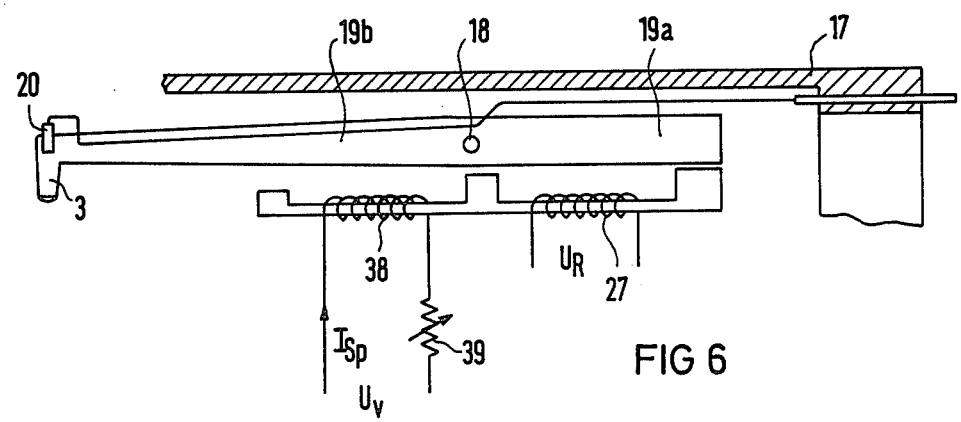
FIG. 6 is a side view, partly in section, of the operative components of a further embodiment of the invention utilizing two drive coils.

Another embodiment of the invention is shown in FIG. 6 wherein forward motion of the lever 19 is electro-magnetically controlled by means of a separate drive coil 38 disposed adjacent to the oscillating lever section 19b. In this embodiment, both the sections 19a and 19b of the lever consists at least in part of low magnetic retentive material. In the embodiments utilizing only one drive coil, only the section adjacent that drive coil (the rear section 19a) need be comprised at least in part of low magnetic retentive material. In the embodiment shown in FIG. 6, the control currents for each of the coils 27 and 38 are supplied from the control unit 12 (corresponding to a forward motion voltage $U_v$ and a return motion voltage $U_R$). The control currents are alternately supplied to the two electro-magnets in the form of current pulses so that the aforementioned reciprocating motion of the lever 19 is achieved. The velocity of the lever 19 in the forward direction can be controlled by an electrical servo component 39 interconnected in the circuit for the drive coil 38.

This embodiment may also include the features described in connection with FIG. 2 of one or more light sources in the form of miniature incandescent lamps or a light conductor disposed in the proximity of the test head 3 in order to further simplify use of the instrument for the user.

Such light sources are disposed such that the imerging light beam is sharply focused and is in the form of a round light spot on the test subject when the end phase 10 (FIG. 2) of the instrument is aligned parallel to the object. The user can thus perceive whether he or she is holding the instrument such that the impact motion will occur perpendicular relative to the axis of the object to be tested. Given deviations from such a perpendicular attitude, the light spot will assume an eliptical shape, thus indicating to the user that the attitude of the instrument should be corrected.

Although the invention has been described with respect to preferred embodiments, it is not to be so limited as changes and modifications can be made which are within the full intended scope of the invention as defined by the appended claims.

I claim as my invention:

1. A percussion instrument comprising:
   a housing;
   a lever pivotally mounted in said housing at a center of gravity of said lever, said lever pivoting about an axis of rotation which is perpendicular to a longitudinal axis of said instrument, said lever carrying a test head at one end thereof extending perpendicularly relative to said longitudinal axis;
   a drive means for accelerating said lever and said test head from an initial position to free flight at constant velocity toward an object to be tested by the reactive rebound of said test head there against;
   an acceleration pickup comprised of at least one piezo-cereamic wafer disposed at a portion of said oscillating lever adjacent said test head, said acceleration pickup being mounted at a location such that a majority of the mass of said lever operates on said piezo-ceramic wafer as an inertial force upon impact of said test head against an object to be tested; and
   an electro-magnetic means for acting on said lever to return said lever to said initial position after impact against said test object.

2. A percussion instrument as claimed in claim 1 wherein said axis of rotation divides said lever into a front section and a rear section, said front section carrying said test head at an end thereof and being longer than said rear section.

3. A percussion instrument as claimed in claim 1 wherein said acceleration pickup is carried at said test head and having leads connected thereto which are conducted along said lever and departing from said lever in the region of said axis of rotation.

4. A percussion instrument as claimed in claim 1 wherein said drive means is a spring engaging a portion of said lever carrying said test head, said spring accelerating said lever from said initial position to a designated velocity, and said housing including a detent means for limiting motion of said spring such that said lever is decoupled from said spring upon reaching said designated velocity.

5. A percussion instrument as claimed in claim 4 further comprising an adjustment means mounted in said housing for mechanically adjusting the tension of said spring.

6. A percussion instrument as claimed in claim 5 wherein said spring is a leaf spring and wherein said adjustment means consists of a slide displaceably mounted in said housing and carrying a pin pressing against said leaf spring with varying pressures as said slide is displaced.

7. A percussion instrument as claimed in claim 1 wherein said drive means is an electro-magnetic drive means combined with said electro-magnetic means for controlling forward and return motion of said lever with respect to a test object.

8. A percussion instrument as claimed in claim 7 wherein portions of said lever adjacent said drive means and said electro-magnetic means at least partially consist of low magnetic retentive material and wherein said drive means and said electro-magnetic means each include an electro-magnetic coil mounted in said housing, each of said electro-magnetic coils being connected to a control unit for alternately supplying drive current pulses to said coils for oscillating said lever.

9. A percussion instrument as claimed in claim 8 further comprising a servo component interconnected with said drive coil in said drive means for varying the drive force applied to said lever.

10. A percussion instrument as claimed in claim 1 wherein a portion of said lever facing away from said test head consists at least partially of low magnetic retentive material, and wherein said electro-magnetic means includes an electro-magnetic coil disposed in said instrument housing adjacent to said section of low magnetic retentive material, said instrument further comprising a permanent magnet carried on said lever in the area occupied by the magnetic field of said electro-magnetic coil, said electro-magnetic means further comprising a means for supplying periodic drive current pulses of alternating polarity to said electro-magnetic coil for alternately repelling and attracting said permanent magnet for oscillating said lever.

11. A percussion instrument as claimed in claim 1 further comprising an illumination means mounted in said housing at a location at which said test head exists said housing, said illumination means generating a sharply focused light spot which is circular in planes perpendicular to the direction of movement of said test head.

12. A percussion instrument as claimed in claim 1 further comprising a detent disposed in the range of movement of said lever during acceleration thereof and said acceleration pickup is carried by said lever and connected to an amplifier means, said instrument further comprising a comparator for comparing a signal from said amplifier with a rated value for the velocity of said lever, and a means for generating a signal upon deviation of the signal from said amplifier from said rated value.

13. A percussion instrument as claimed in claim 12 wherein said means for generating a signal is an optical display means.

14. A percussion instrument as claimed in claim 12 wherein said means for generating a signal is a means for generating an acoustical signal.

15. A percussion instrument as claimed in claim 12 wherein said display means is an optical display means in the form of a lamp disposed on said housing.

* * * * *